(12) United States Patent
Patil et al.

(10) Patent No.: US 8,445,698 B2
(45) Date of Patent: May 21, 2013

(54) PROCESS FOR THE PREPARATION OF AN INTERMEDIATE OF TADALAFIL

(75) Inventors: Dattatray B. Patil, Kolhapur (IN); Killol Patel, Janagadh (IN); Ashok Prasad, New Delhi (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 12/666,606

(22) PCT Filed: Jun. 28, 2008

(86) PCT No.: PCT/IB2008/052609
§ 371 (c)(1),
(2), (4) Date: May 10, 2010

(87) PCT Pub. No.: WO2009/004557
PCT Pub. Date: Jan. 8, 2009

(65) Prior Publication Data
US 2010/0228030 A1    Sep. 9, 2010

(30) Foreign Application Priority Data
Jun. 29, 2007 (IN) .......................... 1402/DEL/2007

(51) Int. Cl.
*C07D 487/00* (2006.01)
(52) U.S. Cl.
USPC .......................................... 548/429; 549/469
(58) Field of Classification Search
USPC .......................................... 548/429; 549/469
See application file for complete search history.

(56) References Cited

U.S. PATENT DOCUMENTS

| | | | | |
|---|---|---|---|---|
| 3,931,219 | A | * | 1/1976 | Aoki et al. ................. 548/303.7 |
| 5,859,006 | A | | 1/1999 | Daugan |
| 2006/0258865 | A1 | | 11/2006 | Deshpande et al. |
| 2006/0276652 | A1 | | 12/2006 | Dolitzky et al. |

FOREIGN PATENT DOCUMENTS

| | | |
|---|---|---|
| WO | WO 2004/011463 | 2/2004 |
| WO | WO 2005/068464 | 7/2005 |
| WO | WO 2006/110893 | 10/2006 |

OTHER PUBLICATIONS

Taher, et al., "Phosphodiesterase Activity in Human Cavernous Tissue and the Effect of Various Selective Inhibitors", *Journal of Urology*, section 285:285A (1993).
Murray, "Phosphodiesterase $V_A$ Inhibitors", *Drug News and Perspectives*, 6(3):150-156 (1993).
Gremmen, et al., "Enantiopure Tetrahydro-beta-carbolines Via Pictet-Spengler Reactions with N-Sulfinyl Tryptamines", *Organic Letters, American Chemical. Society*, Columbus, OH, 2(13):1955-1958 (2000).

* cited by examiner

*Primary Examiner* — Douglas M Willis

(57) ABSTRACT

The present invention relates to a process for the preparation of cis-intermediate of Formula II, Formula II which is useful synthetic intermediates in the preparation of tadalafil.

2 Claims, No Drawings

PROCESS FOR THE PREPARATION OF AN INTERMEDIATE OF TADALAFIL

FIELD OF THE INVENTION

The present invention relates to a process for the preparation of cis-intermediate compound of Formula II,

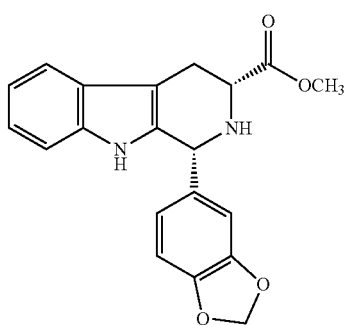

Formula II which is useful synthetic intermediate for the preparation of Tadalafil of Formula I-a

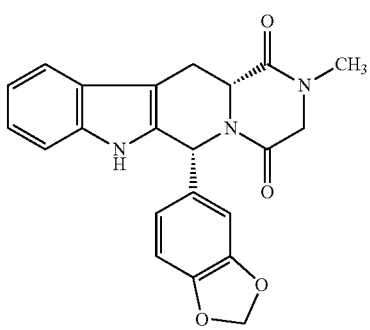

Formula I potent, selective and reversible inhibitor of cyclic guanosine 3',5'-monophosphate specific phosphodiesterase type 5 enzyme having phosphodiesterase inhibitory activity.

BACKGROUND OF THE INVENTION (6R,12aR) 6-(1,3-benzodioxol-5-yl)-2,3,6,7,12,12a-hexahydro-2-methylpyrazino [1',2':1,6] pyrido[3,4-b]indole-1,4-dione (a compound of Formula I) also known as tadalafil, is a potent, selective and reversible inhibitor of cyclic guanosine 3',5'-monophosphate specific phosphodiesterase type 5 enzyme (cGMP specific PDE5).

The biochemical, physiological and clinical effects of cyclic guanosine 3',5'-monophosphate specific phosphodiesterase (cGMP-specific PDE) inhibitors suggest their utility in a variety of disease states in which modulation of smooth muscle, renal, hemostatic, inflammatory, and/or endocrine function is desired. Type 5 cGMP-specific phosphodiesterase (PDE5) is the major cGMP hydrolyzing enzyme in vascular smooth muscle and its expression in penile corpus cavernosum has been reported (Taher et al., *J. Urol.*, 285A: 149 (1993)). PDE5 is an attractive target in the treatment of sexual dysfunction (Murray, *Drug News and Perspectives*, 6(3):150-156 (1993)).

U.S. Pat. No. 5,859,006 (hereinafter the '006 patent) discloses a class of β-carboline compounds, which are useful in the treatment of conditions wherein inhibition of PDE5 is desired. The '006 patent discloses two synthetic pathways for preparation of tadalafil. Path (I) involves Pictet-Spengler reaction of D-tryptophan methyl ester with piperonal leading to the formation of a mixture of cis- and trans-tetrahydro β-carboline intermediates of Formula II and IIB (hereinafter the cis-intermediate of Formula II and trans-intermediate of Formula IIB respectively) in a 3:2 ratio.

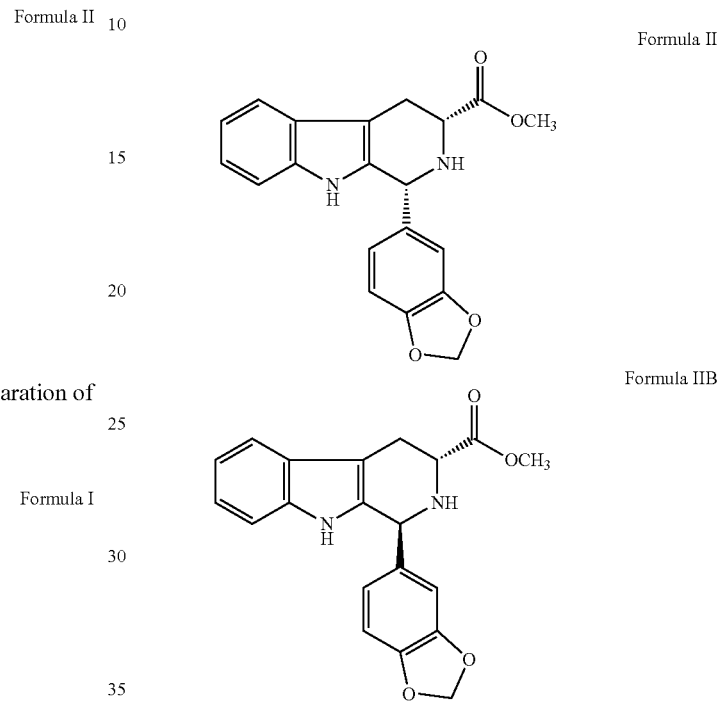

The cis-intermediate of Formula II is then converted to tadalafil in two steps. However, the '006 patent process involves longer reaction times and the yield of the cis-intermediate of Formula II (the desired isomer) is poor and, additionally, it has to be separated from the trans-intermediate of Formula IIB. Moreover, the Pictet-Spengler reaction in path (I) described above, is carried out in the presence of trifluoroacetic acid which is a highly corrosive and hazardous reagent. Path (II) starts with the reaction of D-tryptophan methyl ester with piperonoyl chloride and involves four steps to prepare the cis-intermediate of Formula II. Though this a better yielding process but it is cumbersome as it involves many synthetic steps.

WO 2004/11463 discloses a process for preparation of the cis-intermediate of Formula II wherein D-tryptophan methyl ester hydrochloride is reacted with piperonal in isopropanol. The use of isopropanol in the above reaction requires control of reaction temperature on account of its low boiling point and low flash point. Isopropanol may also be contaminated with peroxides which can cause undesired side reactions. As a result, it is desirable to employ solvents which are easier to handle.

WO 2005/068464 discloses a process for preparation of the cis-intermediate of Formula II wherein the reaction of D-tryptophan methyl ester hydrochloride with piperonal is carried out in the presence of molecular sieves.

U.S. Patent Application No. 2006/0276652 discloses a process for preparation of the cis-intermediate of Formula II wherein D-tryptophan methyl ester hydrochloride is reacted with piperonal in ethyl acetate in the presence of trifluoroacetic acid.

U.S. Patent Application No. 2006/0258865 discloses a process for preparation of the cis-intermediate of Formula II wherein D-tryptophan methyl ester hydrochloride is reacted with piperonal in dimethyl acetamide with or without the use of a dehydrating agent. The work up process involves additional acid-base treatment which can be done away with.

BRIEF SUMMARY OF THE INVENTION

The present inventors observed that by a judicious selection of the reaction solvent and reaction temperature, the cis-intermediate of Formula II,

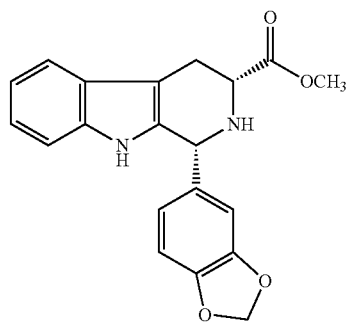

Formula II can be directly isolated from the reaction mass, while the corresponding trans-isomer (hereinafter the trans-isomer) which is undesired, remains in solution. Further, the present inventors observed that at elevated reaction temperature, the undesired trans-isomer converts to the cis-intermediate of Formula II. The present process is diastereoselective, provides good yield and purity of the cis-intermediate of Formula II and at the same time enables removal of the trans-isomer. The present process is industrially useful as it is amenable to scale-up and does not require the use of a dehydrating agent or hazardous chemical like trifluoroacetic acid.

DETAILED DESCRIPTION OF THE INVENTION

A first aspect of the present invention provides a process for the preparation of the cis-intermediate of Formula II,

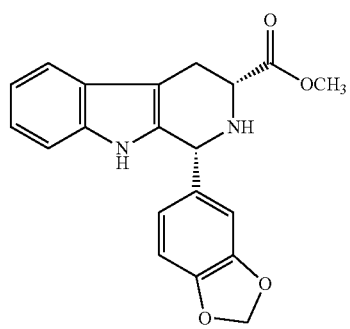

Formula II wherein the process comprises,
  reacting a D-tryptophan compound of the Formula III or a pharmaceutically acceptable salt thereof,

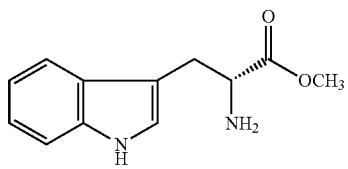

Formula III with a compound of the Formula IV,

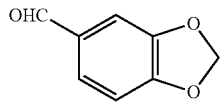

Formula IV in the presence of sulfolane.

D-tryptophan compound of Formula III and the compound of Formula IV are suspended in sulfolane at about 20-40° C. The reaction mixture is heated to about 50-100° C. (e.g., about 70-90° C.), stirred for 10-18 hours and then cooled to about 20-40° C. whereby the cis-intermediate of Formula II starts separating from the reaction mass as a solid which can be filtered and dried. To facilitate the isolation of the cis-intermediate of Formula II, a second solvent can be optionally added.

The D-tryptophan compound of Formula III above can be prepared from D-tryptophan by methods known in the art or as exemplified in the present invention. The aldehyde of Formula IV is commercially available from Sigma Aldrich. Suitable second solvents can be selected from the group consisting of halogenated hydrocarbons, aliphatic hydrocarbons and aromatic hydrocarbons or mixtures thereof. Halogenated hydrocarbons can be selected from the group consisting of dichloromethane, dichloroethane, chloroform, carbon tetrachloride and the like or mixtures thereof. In a preferred embodiment of the present invention, the second solvent is dichloromethane. Aliphatic hydrocarbons can be selected from the group consisting of n-pentane, n-hexane, cyclohexane and the like or mixtures thereof. Aromatic hydrocarbons can be selected from the group consisting of benzene, toluene and the like or mixtures thereof.

Further, unless otherwise specified, any modifications in the reaction conditions of the present invention such as heating temperature, cooling temperature, time or amount of solvent are envisaged within the scope of the instant invention.

A second aspect of the present invention provides a process for the preparation of tadalafil represented by Formula I,

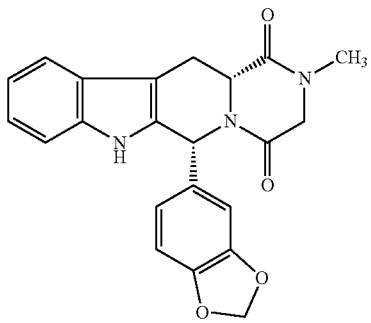

Formula I wherein the process comprises,
  a) reacting D-tryptophan compound of Formula III or a pharmaceutically acceptable salt thereof,

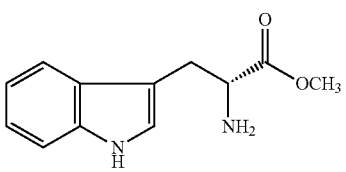

with a compound of Formula IV,

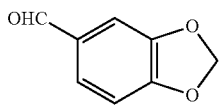
Formula IV in the presence of sulfolane, to obtain the cis-intermediate compound of Formula II,

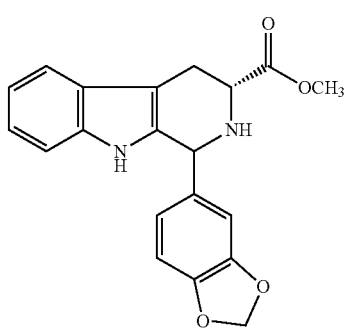
Formula II b) optionally isolating the cis-intermediate compound of Formula II, c) reacting the cis-intermediate compound of Formula II with a compound of Formula V,

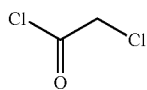
Formula V in the presence of a base to obtain a compound of Formula VI,

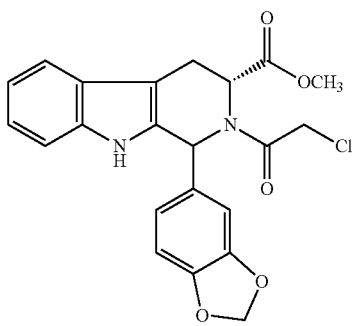
Formula VI d) reacting the compound of Formula VI with a compound of Formula VII,

Formula VII e) isolating tadalafil of Formula I from the reaction mass thereof.

The cis-intermediate of Formula II can be prepared by the method disclosed in the first aspect of the present invention. The cis-intermediate of Formula II can be optionally isolated by addition of a second solvent and then converted to tadalafil of Formula I by methods known in the art (e.g. U.S. Pat. No. 5,859,006, WO 2004/11463).

Suitable second solvents have already been defined in the first aspect of the present invention. Suitable bases can be selected from the group consisting of alkali and alkaline earth metal hydroxides, carbonates, bicarbonates and the like or mixtures thereof. For example, the base can be selected from the group consisting of sodium carbonate, potassium carbonate, sodium bicarbonate, potassium bicarbonate and the like or mixtures thereof.

In another embodiment of the present invention, the cis-intermediate of Formula II is (1R,3R)-1-benzo[1,3]dioxol-5-yl-2,3,4,9-tetrahydro-1H-beta-carboline-3-carboxylic acid methyl ester.

In another embodiment of the present invention, the compound of Formula I is (6R,12aR) 6-(1,3-benzodioxol-5-yl)-2,3,6,7,12,12a-hexahydro-2-methylpyrazino [1',2':1,6] pyrido[3,4-b]indole-1,4-dione.

While the present invention has been described in terms of its specific embodiments, certain modifications and equivalents will be apparent to those skilled in the art and are intended to be included within the scope of the present invention.

EXAMPLE

Step 1: Preparation of D-tryptophan methyl ester hydrochloride

D-tryptophan (100 g) was suspended in methanol (500 mL) and the suspension added to a solution of thionyl chloride (82.14 g) in methanol (500 mL) at 25-30° C. under nitrogen atmosphere. The resultant solution was stirred at reflux for 3 to 4 hours and the reaction mixture was concentrated to a residual volume of 150 mL. To the concentrated mixture dichloromethane (700 mL) was added and the resultant solution was cooled to 0-5° C. with continuous stirring for 0.5 hours. The solid so obtained was filtered, washed with dichloromethane (200 mL) and dried in air at 40-45° C. to afford D-tryptophan methyl ester hydrochloride.

Yield: 100 g (80%)

Step 2: Preparation of Cis 1-benzo[1,3]dioxol-5-yl-2,3,4,9-tetrahydro-1H-beta-carboline-3-carboxylic acid methyl ester hydrochloride D-tryptophan methyl ester hydrochloride (100 g) and piperonal (65 g) were suspended in sulfolane (500 mL) at 25-30° C. The reaction mixture was heated to 80-85° C., stirred for 14 hours and then cooled to 25-30° C. To the cooled mixture dichloromethane (500 mL) was added and the resultant mixture stirred continuously for 1 hour. The solid obtained was filtered, washed with dichloromethane (500 mL) and dried in air at 40-45° C. to afford cis 1-benzo [1,3]dioxol-5-yl-2,3, 4,9-tetrahydro-1H-beta-carboline-3-carboxylic acid methyl ester hydrochloride.
Yield: 135 g (89%)
Purity: >98% (by HPLC)
Trans-isomer content: <0.5% (by HPLC)

Step 3: Preparation of cis 1-benzo[1,3]dioxol-5-yl-2-(2-chloro-acetyl)-2,3,4,9-tetrahydro-1H-beta-carboline-3-carboxylic acid methyl ester Cis 1-Benzo[1,3]dioxol-5-yl-2,3,4,9-tetrahydro-1H-beta-carboline-3-carboxylic acid methyl ester hydrochloride (50 g) was dissolved in dichloromethane and 5% aqueous sodium bicarbonate (500 mL). The organic layer was separated and washed with deionized water (500 mL). The organic layer was added into deionized water (50 mL) and treated with sodium bicarbonate (15 g) at 25-30° C. To the resultant mixture chloroacetyl chloride (25 g) in dichloromethane (50 mL) was added at a rate sufficient to maintain the temperature of the reaction mixture between 0 and 5° C. The reaction mixture was stirred for three hours. After the completion of reaction, dichloromethane (500 mL) and DI water (1 L) were added. The organic layer was separated and washed sequentially with water followed by aqueous sodium bicarbonate solution till pH was 6.5-7.0, and finally with water. The organic layer was concentrated under reduced pressure to obtain a solid. The solid was dissolved in acetone (750 mL) and the resultant solution was concentrated to a residual volume of about 75 mL. To the concentrated solution, deionized water was slowly added at 20-25° C. and the resultant mixture cooled to 0-5° C. with continuous stirring for 0.5 hours. The solid so obtained was filtered and dried to afford cis 1-benzo[1,3]dioxol-5-yl-2-(2-chloro-acetyl)-2,3,4,9-tetrahydro-1H-beta-carboline-3-carboxylic acid methyl ester.
Yield: 48.5 g (88%)

Step 4: Preparation of (6R,12aR) 6-(1,3-benzodioxol-5-yl)-2,3,6,7,12,12a-hexahydro-2-methylpyrazino [1',2':1,6] pyrido[3,4-b]indole-1,4-dione (tadalafil)

Cis-1-benzo[1,3]dioxol-5-yl-2-(2-chloro-acetyl)-2,3,4,9-tetrahydro-1H-beta-carboline-3-carboxylic acid methyl ester (30 g) was taken in methanol (450 ml). The resultant mixture was heated to 35-40° C. and aqueous methyl amine (27 ml; 40%) was added. The reaction mixture was stirred at 50-55° C. for 5 hours and then cooled to 10-15° C. with continuous stirring for 0.5 hours. The solid so obtained was filtered and dried to afford (6R,12aR) 6-(1,3-benzodioxol-5-yl)-2,3,6,7,12,12a-hexahydro-2-methylpyrazino [1',2':1,6] pyrido[3,4-b]indole-1,4-dione.
Yield: 24.6 g (90%)
Purity: 99.9% (by HPLC)

What is claimed is:

1. A process for the preparation of the cis-intermediate of Formula II,

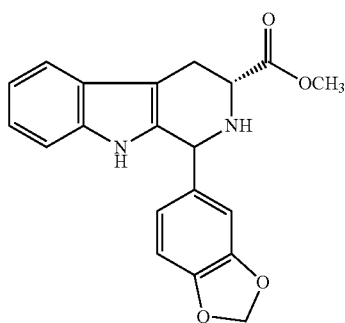

Formula II wherein the process comprises,
reacting a D-tryptophan compound of the Formula III or a pharmaceutically acceptable salt thereof,

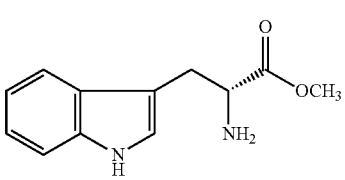

Formula III with a compound of Formula IV,

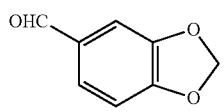

Formula IV in the presence of sulfolane.

2. The process according to claim 1 wherein the process is carried out at a temperature of 50-100° C.

* * * * *